United States Patent [19]
Jansen

[11] Patent Number: 5,977,443
[45] Date of Patent: Nov. 2, 1999

[54] APHID RESISTANCE IN COMPOSITES

[75] Inventor: Johannes Petrus Antonius Jansen, Zwijndrecht, Netherlands

[73] Assignee: Rijk Zwaan Zaadteelt en Zaadhandel B.V., Netherlands

[21] Appl. No.: 08/748,212

[22] Filed: Nov. 12, 1996

[30] Foreign Application Priority Data

Jun. 4, 1996 [NL] Netherlands .................. 1003261

[51] Int. Cl.$^6$ .................. A01H 5/00; A01H 1/04
[52] U.S. Cl. .................. 800/305; 800/298; 800/265; 800/269
[58] Field of Search .................. 800/200, 205, 800/220, 230, 250, 255, DIG. 11, DIG. 13, 269, 265, 298, 305; 47/58, DIG. 1

[56] References Cited

PUBLICATIONS

Michelmore, R., "Molecular Approaches to Manipulation of Disease Resistance Genes" Annu Rev. Phytopathol., 1995, vol. 15, pp. 393–427.

Vos, Pieter et al., "AFLP: a new technique for DNA fingerprinting," Nucleic Acids Research, 1995 vol. 23, No. 21, pp. 4407–4414.

Winter, P. et al., "Molecular marker technologies for plant improvement," World Journal of Microbiology & Biotechnology, 1995, vol. 11, pp. 438–448.

Michelmore, Richard W. et al., "Genetic mapping in lettuce," In: R.L. Phillips & I.K. Vasil (eds.) DNA–based markers in plants, Kluwer Acad. Publishers, Dordrecht, 1994, pp. 223–239.

Lefebvre, V. et al., "Tools for marking plant disease and pest resistance genes: a review," Agronomie 15, 1995, vol. 1, pp. 3–19.

Dunn, J.A. et al., Tests of Agrochemical and Cultivars, No. 1, 1980, (Ann. Appl. Biol. 94, Supplement) pp. 58–59.

Briggs, F.N. et al., "Principles of Plant Breeding," Introduction to Plant Breeding, 1967, pp. 162–174.

Eenink, A.H. et al., Inheritance of Resistance to the Leaf Aphid *Nasonovia ribis–nigri* in the Wild Lettuce Species Lactucavirosa, Euphytica, vol. 32, 1983, pp. 691–695.

Smith, John M. et al., "A new source of resistance to downy mildew," The Grower, 1989, pp. 54–55.

Eenink et al. Resistance of lettuce (Lactuca) to the leaf aphid *Nasonovia ribis nigri* 1. Transfer of resistance from *L. virosa* to *L. sativa* by interspecific crosses and selection of resistance breeding lines. Euphytica. vol. 31. pp. 291–299, 1982.

*Primary Examiner*—Douglas W. Robinson
*Assistant Examiner*—Melissa L. Kimball
*Attorney, Agent, or Firm*—Webb Ziesenheim Logsdon Orkin & Hanson, P.C.

[57] ABSTRACT

A plant in the Compositae family in which the Nr gene, for resistance to *Nasonovia ribisnigri* (a troublesome lettuce aphid) is present without any associated genetic information responsible for "Compact growth and Rapid Aging," or CRA, at least to the extent that the CRA phenotype is not expressed. The resistance gene preferably originates from *L. virosa*. The removal or change of the genetic information resulting in the CRA phenotype is caused by recombination event(s) in the vicinity of the gene. Plants are generally selected in which one or more recombination events have taken place, either in the same or in successive generations. Such recombination events may be accomplished either by meiotic crossing-over or by the use of molecular biology tools such as the AFLP technique known in the art.

13 Claims, 1 Drawing Sheet

APHID RESISTANCE IN COMPOSITES

BACKGROUND OF THE INVENTION

1. Field of the Invention

The present invention relates to new plants of the family Compositae, in particular lettuce plants of the genus Lactuca which are resistant to the aphid *Nasonovia ribisnigri* and herein display agronomically desirable traits.

2. Description of the Related Art

Aphids cause much damage in vegetable cropping. They feed on the phloem of the plants and thereby cause reduced or abnormal growth. Living aphids or aphid remnants make the harvested product unsaleable. In addition, honeydew, a sugary liquid secreted by the aphids, forms a sticky layer on the leaves. Aphids are greatly feared, not only because of this direct damage, but also because they spread virus diseases.

*Nasonovia ribisnegri* is the aphid species which in Europe is found most frequent on lettuce grown in the field. *N. ribisnigri* is particularly harmful because it prefers to feed on the young leaves of the plant. The aphids hereby become easily trapped in the closing lettuce heads, making them difficult to reach for pesticides. Especially in the crisphead types of lettuce, which form a tight head, this causes great problems. Crop farmers limit the damage caused by aphids by repeatedly spraying pesticides on the growing crops, in particular when the weather conditions are favourable for the reproduction of aphids. The use of excessive quantities of pesticide is undesirable from an environmental viewpoint. Pesticides moreover miss their target in particular cases, as described above for instance in the case of closing lettuce heads.

Resistance of the plants on which aphids occur (host plant resistance) is an environmentally-friendly alternative for the use of pesticides to control the development of aphids in for instance lettuce. Therefore extensive research has already been done into resistance to *N. ribisnigri* and into the inheritance of this type of resistance. For a number of lettuce cultivars a partial resistance to *N. ribisnigri* was described (Dunn, J. A. & Kempton, D. P. H.(1980) Tests of Agrochemical and Cultivars, No. 1, (Ann, appl. Biol. 94, Supplement): 58–59). An almost complete resistance to *N. ribisnigri* was found in the wild Lactuca variety *L. virosa* L. (Eenink A. H. & F. L. Dieleman (1983) Euphytica 32:691–695). This Nasonovia resistance in *L. virosa* was found to be caused by a single dominant gene, which is called Nr gene.

In 1981 *L. sativa* plants were released by the former Institute for Horticultural Plant Breeding (IVT, now part of CPRO-DLO) in Wageningen which contained in their genome an *L. virosa* chromosome fragment having the Nr gene for resistance to *N. ribisnigri*. These plants resulted from a hybridization program with *L. virosa* and *L. sativa*, in which *L. serriola* was used as bridge species. A bridge species is used when two species can only be crossed with one another to a limited extent, as was the case with *L. virosa* and *L. sativa*.

The released plants were of an undesirable type in respect of phenotype and agronomic traits (non-heading, poor cultivation characteristics).

Because of the undesirable agronomic traits these plants were used by breeding companies as hybridization parent for the purpose of obtaining plants by genetic recombination and selection, which combine resistance to *N. ribisnigri* with good agronomic traits.

*L. sativa* is an annual species but, when it is cultivated under artificial light at an increased temperature, 2–5 successive generations can be produced within a year. Backcrossing procedures are a generally known and suitable method for crossing genes from a "donor parent" into a genetic background with a high agronomic value. In general the introgression of a dominant gene into an agronomically acceptable phenotype can be achieved by 3–5 backcrosses, followed by 2–3 self-pollinations. 5–8 generations in 3–5 years are therefore required to obtain agronomically acceptable plants having the desired gene in their genome. However, although plants having the Nr gene were already released in 1981 to seed companies, the successful transfer of the Nr gene to agronomically acceptable lettuce plants has so far not yet been reported.

It is now the object of the present invention to provide plants of the family Compositae, and in particular new lettuce plants, which combine resistance to aphids of the species *Nasonovia ribisnigri* with agronomically good traits.

This object is achieved according to the invention in that it was found in the course of a selection program that the application of this resistance in lettuce plants having good agronomic characteristics was prevented by negative side-effects caused by the *L. virosa* chromosome fragment, on which the Nr gene was situated, when it was inserted in an *L. sativa* genome. Compared with cultivated lettuce plants without the *N. ribisnigri* resistance, plants which were homozygous for the Nr gene in fact displayed a reduced growth, a lighter green color and accelerated degradation of chlorophyll in the older leaves of the generative plant (when the plant is bolting). This resulted in generative plants having completely or partially white older leaves and/or reduced plant height. This agronomically undesired phenotype will be further designated in this application as "CRA phenotype", meaning "Compact growth and Rapid Ageing". FIG. 1 gives an example of the difference between normal lettuce plants and CRA plants. In the vegetative stage the CRA symptoms are particularly apparent when the plants grow under stress (for instance at low temperature).

SUMMARY OF THE INVENTION

The invention therefore provides plants having the Nr resistance gene in the genome, wherein the genetic information responsible for the CRA phenotype is absent from the genome of the plant at least to such an extent that the CRA phenotype is not expressed.

DETAILED DESCRIPTION OF THE PREFERRED EMBODIMENTS

Figure 1:
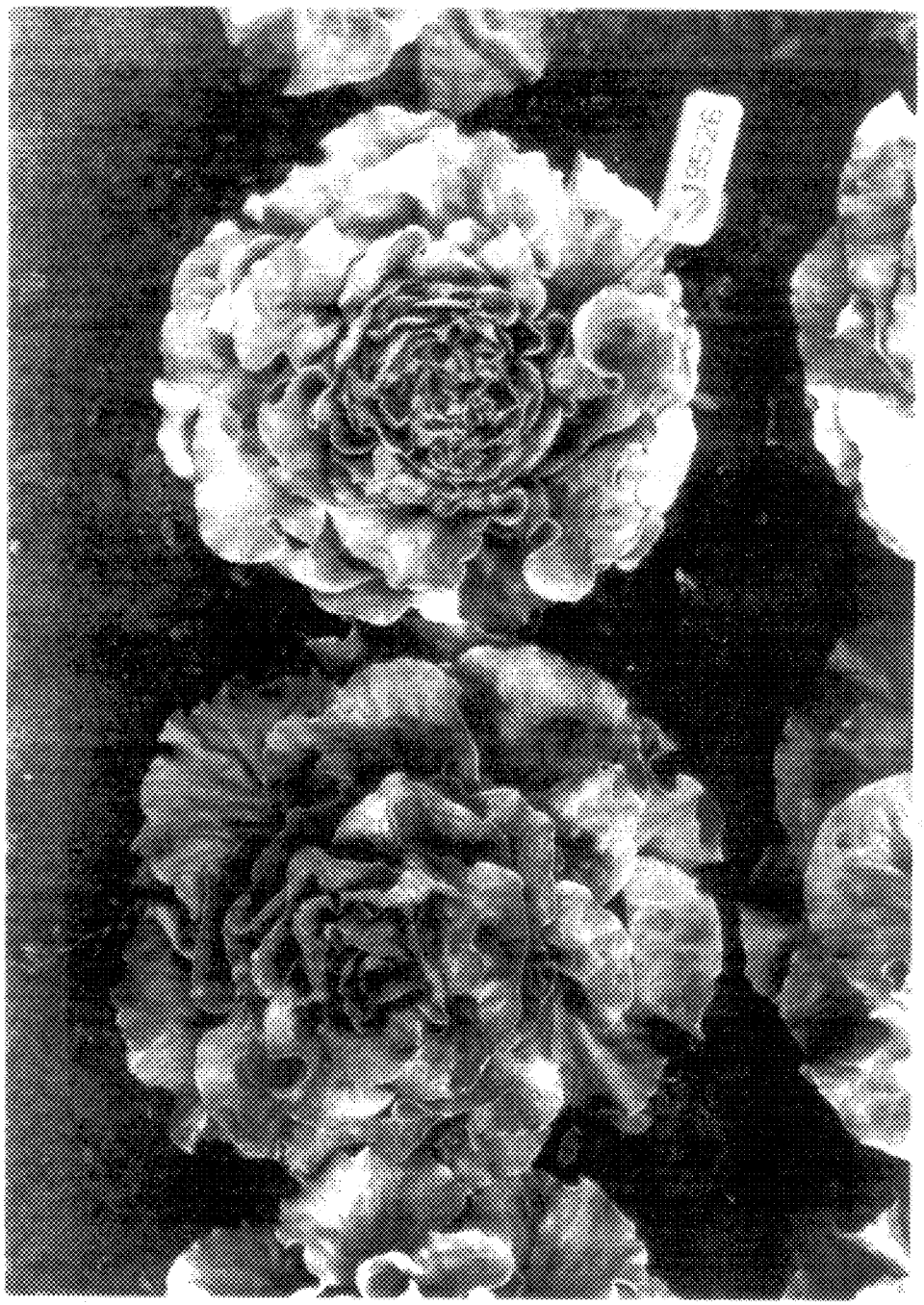
FIG. 1 is a photograph of a plant according to the present invention.

The present invention is based on the insight that the CRA phenotype is not a result of the Nr gene itself, but rather of genetic information from the vicinity of the resistance gene. According to the invention it has therefore been found that there is a link between the resistance and the CRA phenotype. By breaking this link it is possible to grow resistant, agronomically acceptable plants. It has otherwise been found from the literature and from our own research that other traits of *L. virosa* are also often associated with the CRA phenotype when they are crossed into other plants. Maxon Smith and Langton (The Grower, Sep. 21, 1989 p 54–55) describe a link between compact growth and a resistance to *Bremia lactucea*, which was introgressed from

*L. virosa* into cultivated lettuce. The present invention also provides a solution herefor, now that it has been found that the CRA phenotype is genetically linked to the desired trait, The CRA phenotype is a recessive trait which is only expressed in homozygously resistant plants.

Once this insight had been gained it became possible to select plants in which the genetic information for the CRA phenotype was removed from the vicinity of the NR gene or changed to an extent such that the resistance was no longer expressed in combination with the CRA phenotype. Described by way of example in this application is the Nr resistance gene but the principle of the invention also applies of course to other traits linked to CRA which originate from *L. virosa*.

The removal or change of the genetic information resulting in the CRA phenotype is caused by recombination event(s) in the vicinity of the gene. At this moment it is not entirely clear whether the CRA information lies to the left or the right of the gene or around it. When the genetic information for the CRA phenotype lies on both side of the resistance gene, both parts of this genetic information are preferably changed or removed. According to the invention, preferably in the end plants will be selected wherein two or more recombination events have taken place. Such a double recombination event does not of course need to have taken place in one generation, but recombination events from successive generations may also result in the eventual removal or change of the genetic information on both sides of the resistance gene. If the CRA information only lies on one side of the gene a single recombination event is of course sufficient.

In this application a "recombination event" is understood to mean a meiotic crossing-over.

The plants without CRA phenotype can be obtained by means of conventional hybridization techniques. A condition is however that the correct selection criterion is used. According to the invention a suitable selection criterion has now been defined, namely the complete or partial absence or inactivity of a piece of genetic information from the vicinity of the resistance gene. According to the invention it is not relevant how much of the genetic information surrounding the resistance gene is absent from a recombinant or in which manner the CRA gene or the CRA genes is or are deactivated, as long as the CRA phenotype is absent from the plant and its progeny.

In order to find plants in which recombination has taken place between the Nr gene and genes causing the CRA phenotype, segregating populations, or progeny of such populations, are in practice screened for plants having a recombinant phenotype, i.e. homozygous resistance to *N. ribisnigri* in combination with a non-CRA phenotype. Although it is possible to find suitable recombinants in this manner, as can be seen from the examples, there are however a number of reasons why finding agronomically valuable recombinants can be complicated.

In the selection program for combining resistance with good agronomic characteristics it has been found that plants which combine *N. ribisnigri* resistance with an agronomically valuable phenotype are almost always not the result of recombination in a chromosome but are heterozygous for the introgressed *L. virosa* chromosome fragment. According to the invention it was found that the CRA phenotype is inherited recessively. Because the Nr gene is dominant a plant with a single copy of the *L. virosa* chromosome fragment will combine resistance with a normal (non-CRA) phenotype. Progeny of such plants will however segregate for the CRA phenotype and cannot be used commercially, because commercial lettuce varieties are pure lines which must comply with strict requirements of genetic uniformity in order to be brought into circulation. It was further found that, because the expression of the resistance is a biological characteristic depending on different ambient and experimental conditions, a certain fraction of the plants in an *N. ribisnigri* resistance test is often classified incorrectly. Plants with the Nr gene are considered susceptible and plants without the Nr gene are scored resistant. The same applies to scoring of the CRA phenotype of individual plants in the field or in the glasshouse. Depending on the experimental and ambient conditions a certain fraction of plants with the inserted *L. virosa* chromosome fragment will be considered normal in homozygous condition, while a number of the plants wherein the inserted chromosome fragment is present in heterozygous condition or is totally absent, could display symptoms resulting in an erroneous classification of the CRA phenotype.

Despite the above described difficulties which may occur, it will be apparent from the examples that the selection of the desired plants in which the genetic information for the CRA phenotype is absent is very much possible in the conventional manner. This manner of selection does however require a relatively large segregating population or a large number of hybridizations.

It may therefore be more efficient to make use of molecular biological tools in the selection of suitable plants. An exceptionally useful technique is the AFLP technique, as described by Vos, P. et al., in Nucleic Acids Research, 1995, Vol. 23, No. 21: 4407–4414. When applied to the present invention this technique is based on mapping DNA markers which are genetically linked to the Nr gene, whereafter it can be determined in relatively simple manner whether a recombination event has occurred in the vicinity of the Nr gene in a progeny of a hybridization experiment. When a linked marker is missing, a crossing-over between the Nr gene and that marker has (therefore) taken place. By choosing markers at various distances from the gene it can also be determined whether much or little has disappeared from the vicinity of the gene. Progeny wherein one or more of the linked markers is absent are therefore lacking at least a piece of the undesired vicinity of the gene and therefore have a more than average chance that a chromosome with the Nr gene is present, wherein the genetic information resulting in the CRA phenotype is absent. The efficiency of the selection of plants combining homozygosity for the Nr gene with absence of the CRA phenotype can be significantly increased with molecular markers.

Mapping of genetic markers in the vicinity of a gene is a procedure which can be performed quite easily by the average molecular-biological skilled person and which is for instance described in Lefebvre, V. & A. M. Chevre. Tools for marking plant disease and pest resistance genes: a review. Agronomie 15, 1995 (1): 3–19; Michelmore, R. W. Molecular approaches to manipulation of disease resistance genes. Annual Review of Phytopathology 33 (1995): 393–427; Michelmore, R. W., R. V. Kesseli & E. J. Ryder. Genetic mapping in lettuce. In: R. L. Phillips & I. K. Vasil (eds.) DNA-based markers in plants, Kluwer Acad. Publishers, Dordrecht, 1994, pp. 223–239; Winter, P. & G. Kahl. Molecular marker technologies for plant improvement. World Journal of Microbiology & Biotechnology, 1995, 11 (4); 438–448. General information concerning AFLP technology can be found in Vos, P. et al. (supra). In Example 2 the use of the AFLP technology for selecting plants according to the invention will be further elucidated.

The present invention is illustrated in this application with reference to the cultivated lettuce Lactuca sativa. It will be apparent to the skilled person that the principles of the invention are likewise applicable to other species of the genus Lactuca, and more generally to plants of the family Compositae. Reference to L. sativa should not therefore be interpreted as a limitation of the invention.

According to the present invention the resistance gene preferably originates from L. virosa. Plants according to the invention are of course substantially completely fertile and homozygous for the resistance gene. Due to the absence of the genetic base resulting in the CRA phenotype they exhibit substantially no reduced growth, no reduced green colouring of the leaves and no premature chlorophyll degradation when the plants are in the generative phase.

"Cultivated lettuce" or "cultivated lettuce plants" are understood to mean lettuce which is suitable for consumption and meets the requirements for commercial cultivation. In addition to the lettuce plants themselves, and the parts thereof suitable for consumption, such as the heads or leaves, the invention comprises parts or derivatives of the plant suitable for propagation. Examples of parts suitable for propagation are organ tissues, such as leaves, stems, roots, shoots and the like, protoplasts, somatic embryos, anthers, petioles, cells in culture and the like. Derivatives suitable for propagation are for instance seeds. The plants according to the invention can be cultivated or propagated in the conventional manner but also by means of tissue culture techniques from plant parts.

Plants according to the invention, which are characterized by the absence of a CRA phenotype in the presence of the Nr gene in homozygous condition, can be used to transfer N. ribisnigri resistance into other agronomically valuable lettuce types. This takes place for instance by means of standard backcrossing procedures for a dominant gene (see Briggs, F. N. & P. F. Knowles (1967) In: Principles of plant breeding, pp. 162–167), followed by self-pollination of the plants for at least two generations and the selection of lines which are homozygous for the resistance gene.

In particular steps of the selection program, cross-pollinations are used. However, cross-pollination of self-pollinating plants requires that self-fertilization is prevented in the plant which is used as the female parent. This can be achieved by manually removing the male parts of the reproductive organs. This can be effected by physical removal thereof or by means of chemical agents and/or the use of water on the flowers. All these methods of removing or rendering dysfunctional the male parts of the reproductive organs are well known in the art. Progeny of a hybridization can be obtained by causing the female parent of the hybridization to produce seed, collecting the F1 or backcross seed and sowing it to obtain new plants. F1 plants can be self-pollinated to produce the F2 generation or backcrossed with the recurrent parent of a backcross scheme. Back-crossed plants can be further backcrossed with the recurrent parent to improve the agronomic value of the plants in a subsequent generation or can be self-pollinated to produce plants which are homozygous for the Nr gene.

In a first specific embodiment the invention provides L. sativa L. plants of the line RZ 96.85123, the obtaining of which is further explained in example 2. Plants of this line are homozygous for the Nr gene and lack the genetic information which causes the CRA phenotype. Such plants are not small and/or not yellow, like CRA plants. When plants are not small and/or not yellow, enough of the genetic information causing the CRA phenotype is missing, or this genetic information is sufficiently deactivated. In order to illustrate the invention seeds of the RZ 96.85123 plants were deposited at NCIMB National Collections of Industrial and Marine Bacteria Limited, 23 St. Machar Drive, Aberdeen AB2 1RY, Scotland, United Kingdom) under number 40804 on May 16, 1996. The condition was imposed that until the date of grant of a patent, samples of the deposited seeds can only be issued to a skilled person.

In a another specific embodiment the invention provides the result of the conventional hybridization method and the specific selection scheme as described in example 1 in the form of plants of line RZ 96.75906. These plants are likewise homozygous for the Nr gene and lack the genetic information causing the CRA phenotype. In order to illustrate the invention seeds of the RZ 96.75906 plants were deposited at NCIMB under number 40803 on May 16, 1996.

The invention further relates to a method for obtaining plants according to the invention, comprising of selecting a parent plant which is heterozygous for Nr resistance, manufacturing a segregating population, producing a progeny of substantially each plant of the segregating population, and checking the progeny for resistance and CRA phenotype. A segregating population can be produced in different ways, such as by self-pollination of the heterozygous parent plant, by crossing of the heterozygous parent plant with a resistant plant and by applying a doubled haploid technique to the heterozygous parent plant. In the doubled haploid technique, new plants are cultivated from doubled gametes of a plant. The gametes can originate from the male reproductive organs (androgenesis) or from the female reproductive organs (gynogenesis). The culture of doubled haploids usually requires an in-vitro step. The advantage of doubled haploids in the search for recombinants is that the gametes from which the plants originate result from a meiotic recombination in the heterozygous parent plant, while the resulting doubled haploids are completely homozygous, so that masking effects of heterozygosity are avoided.

In plants obtained via doubled haploid technique the desired recombinant can be immediately recognized: a plant with resistance and without CRA. In the lines obtained by self-pollination of plants from a segregating population lines having desired recombinant plants can be recognized in that the line is uniformly resistant but still segregates for CRA, or in that the line still segregates for resistance but uniformly has a normal phenotype, or in that the line is uniformly resistant and uniformly has a normal phenotype.

The efficiency of said method can be increased significantly when, before producing progeny of substantially each plant, a pre-test takes place on plants in which a desired recombination event has occurred. Such a pre-test can for instance be performed using molecular biological methods, such as the AFLP technique. The selection according to the AFLP technique is based on detecting recombination events in the vicinity of the locus of the Nr gene in the genome of plants from the segregating population.

The present invention will be further elucidated with reference to the accompanying examples, which are only given by way of illustration and are not intended to limit the invention in any way.

EXAMPLES

General

The techniques used to obtain the plants according to the invention are described very generally hereinbelow. The specific details of the experiments performed will be further examined in the examples.

Mterials and Method
1. Resistance Test

Resistance to *N. ribisnigri* can be demonstrated by growing a population of plants and inoculating each plant with a certain number of *N. ribisnigri* aphids (for instance 15). Resistance is proven when after a certain test period (for instance 7 days) the number of aphids on the plant is 0 or less than the original number, while on susceptible plants the number of aphids per plant has increased after the test period.

Plants of a susceptible variety are included in the test as control. The aphids must clearly multiply on these control plants for the test to be accepted as reliable. The test is preferably performed at a temperature between 18 and 24° C. and at a minimum day length of 14 hours. Small plants in the vegetative phase with approximately 1 to 3 real leaves are preferably used for inoculation with *N. ribisnigri* individuals, although older plants can also be used in the resistance test. *N. ribisnigri* resistance is not only observed under test conditions but can likewise be seen in the field or in the glasshouse.

The aphids used in the resistance test were of a red biotype designated WN1 and can be obtained at the Department of Entomology of the Agricultural University of Wageningen. Prior to the test they were cultured on lettuce plants. Green coloured aphids can of course also be used. Resistance tests were performed with seeds which were sown in potting compost blocks. The aphids were transferred to the young lettuce plants four weeks after sowing.

2. Hybridizations

For the first hybridization one parent is used which is homozygous for the resistance to *N. ribisnigri* and which displays the agronomically undesirable traits of reduced growth, reduced green colouring and/or early degradation of chlorophyll in the generative phase. The other plant is a plant which is not resistant to *N. ribisnigri* and does not display the above stated agronomically undesirable traits.

The F1 plants obtained by hybridization can be backcrossed with the recurrent (*N. ribisnigri*-susceptible) parent (or another *N. ribisnigri*-susceptible plant), and/or can be cultured to F2 generation by self-pollination. The thus resulting BC1 (backcrossed) or P2 plants can likewise be cultured to a next generation via self-pollination or can be used again as hybridization parent.

Detecting plants with a recombination event close to the locus of the resistance-providing Nr gene using the AFLP technique or other technique of molecular markers, can efficiently take place in a population segregating for the Nr gene. This can be a population obtained by self-pollination of a heterozygous plant (see Example 2), or a population obtained by backcrossing a heterozygous plant, preferably with a plant from the resistant parent line. Phenotypical selection for recombination between *N. ribisnigri* resistance and CRA phenotype can efficiently take place with a population of inbred lines from plants from a population segregating for the Nr gene.

A line is understood here to mean a group of seeds or plants obtained by self-pollination of a single plant.

The increase in selection efficiency through the use of molecular markers is achieved in that a pre-selection can be carried out with markers. Only progeny of plants in which it has been shown using markers that a recombination event has taken place in the vicinity of the Nr locus are subsequently further tested for resistance and the presence of the CRA phenotype.

Breaking of linkage between resistance and the CRA phenotype can be found in a population of lines (whether or not preselected with markers) by testing a number of plants per line (for instance 25) for resistance to *N. ribisnigri* and by testing the same or different plants (for instance 25) for CRA phenotype. On the basis of these two tests each line can be classified per trait into the following categories:

Resistance:
 a) uniformly resistant
 b) segregating into resistant and susceptible plants
 c) uniformly susceptible CRA phenotype:
 a) uniformly CRA phenotype
 b) segregating into plants with CRA phenotype and plants with normal phenotype
 c) uniformly normal phenotype Recombinant plants, which are homozygous for the Nr gene without having the CRA phenotype, can be found:

1) in lines which are uniformly resistant to *N. ribisnigri* and whereof not all plants have the CRA phenotype, and 2) in lines uniformly having a normal phenotype and whereof not all plants are susceptible to *N. ribisnigri*.

In the first case plants without the CRA type are selected for seed production. Progeny from self-pollination of these selected plants are again tested for resistance and CRA phenotype and lines which are uniformly resistant and uniformly have a normal (non-CRA) phenotype are retained.

In the second case resistant plants are selected for seed production. Progeny from self-pollination of these selected plants are again tested for resistance and CRA phenotype and lines which are uniformly resistant and uniformly have a normal (non-CRA) phenotype are retained.

3. Selection by Means of the AFLP Technique

A small piece of leaf (for instance 50 mg) is collected from each plant for testing and DNA is extracted. In order to carry out a linkage study between AFLP markers and the Nr gene, each sampled plant must also be tested for resistance to *N. ribisnigri*, which can take place according to the above procedure. The detection of AFLP or other molecular markers linked to the Nr gen, can take place by comparing the marker pattern of individual resistant or susceptible plants or by mixing DNA of groups of susceptible or resistant plants (so-called "pools") and comparing the marker patterns of these pools. On the basis of the marker patterns of individual plants from a segregating population, markers linked to the Nr gene can subsequently be ordered in a marker map, indicating the genetic distance between the markers mutually and between the markers and the Nr gene. Methods for detecting the degree of genetic linkage between markers mutually and between markers and a monogenic trait are standard in the state of the art and are described in many handbooks. Computer software for performing these linkage studies is generally available (for instance the program "Joinmap", distributed by the CPRO-DLO in Wageningen).

With a set of markers closely linked to the Nr locus, plants can be detected with one or more recombination events in the vicinity of the Nr locus. Plants with a recombination event are characterized in that a proportion of the markers linked to the Nr gene are replaced by markers from the susceptible parent with normal (non-CRA) phenotype.

The development of markers and marker determinations for this project were carried out by Keygene NV, Agro Business Park 90, Post box 216, 6700 AE, Wageningen. Use was made only of the AFLP technique developed and patented by Keygene. For details of the AFLP technique reference is made to P. Vos et al., AFLP: a new technique for DNA fingerprinting, Nucleic Acids Research, 1995, 23 (21): 4407–4414.

The AFLP technique is now supplied by various suppliers and is available to the average skilled person. For the average skilled person the detection of closely linked markers for a gene has thereby become a routine matter, inasfar as suitable plant populations are available. It will be apparent to the average skilled person that by choosing restriction enzymes and primers many different AFLP markers can be generated which are linked to a certain gene, and that in order to generate a set of closely linked markers with the object of detecting meiotic recombination in the vicinity of a locus, it is not of essential importance which closely linked markers are used for that purpose. Decisive are only the number of markers used plus the distribution over the chromosome fragment in which it is wished to detect recombination.

Example 1

Conventional hybridization
L. sativa L. plants acording to the invention were obtained according to the scheme below:
Line 793202 x BC2 (Calona x R18 donor)

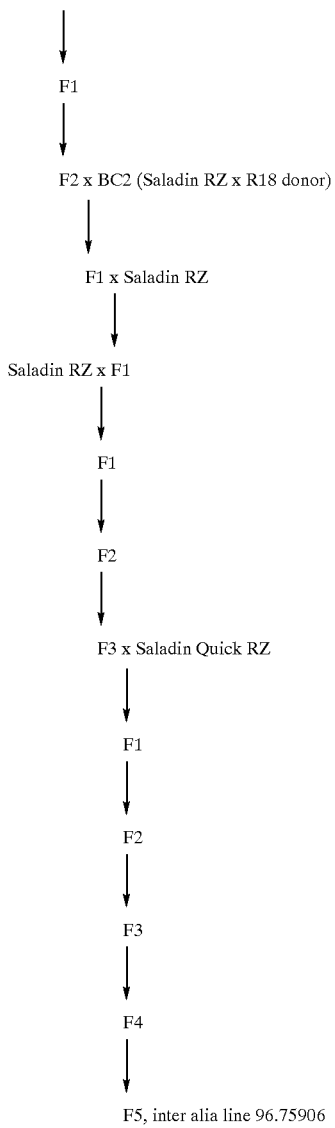

F5, inter alia line 96.75906

A plant from line IVT 793202, one of the lines with the Nr gene, released in 1981 by the former Institute for Horticultural Plant Breeding (IVT) in Wageningen, was crossed with a plant from our own selection line of the crisphead lettuce type with full resistance to the downy mildew disease caused by Bremia lactucae (BC2(Calona x R18 donor)). F1 seed of this cross was sown and propagated to F2. F2 plants were tested for resistance to N. ribisnigri and for morphology, and a selected resistant F2 plant was crossed with a plant of the Saladin type with full resistance to B. lactucae (BC2("Saladin RZ" x R18 donor). F1 plants from this cross were checked for resistance to N. ribisnigri, and backcrossed with a plant of the type "Saladin RZ". F1 plants from this cross were checked for resistance to N. ribisnigri and crossed again with a plant of the type "Saladin RZ". F1 seed of this cross was sown and propagated to F2. F2 plants were checked for resistance to N. ribisnigri and for morphology, and a resistant F2 plant selected for crisphead lettuce type was propagated to F3 line. F3 lines were once again tested for resistance and for phenotype and an F3 plant selected for crisphead lettuce type was crossed with a plant of the type "Saladin Quick RZ". The F1 generation from this cross was checked for resistance to N. ribisnigri and propagated to F2. Plants from the F2, F3 and F4 generations originating from one F1 plant of this hybridization were tested for resistance to N. ribisnigri and for phenotype. Selected F2 and F3 plants combining resistance with a desired non-CRA phenotype, were always found to be heterozygous for the Nr gene. However, in the F4 generation of this cross, finally a line was found which was uniform for the normal (crisphead lettuce) phenotype, i.e. displayed no symptoms of CRA and in addition still segregated for resistance to N. ribisnigri. From a number of plants of this F4 line seed was produced. The progeny of a few of these F4 plants (inter alia line RZ 96.75906) were found to no longer segregate for resistance to N. ribisnigri, and therefore combine homozygosity for the Nr gene with an agronomically valuable phenotype, due to the absence of the CRA symptoms.

It should be noted here that the example described here gives the history of the development and genealogy of plants according to the invention. It by no means shows all the produced generations originating from this series of hybridizations, but only those generations of which the plants of the invention are lineal progeny. Further branches of the hybridization and selection scheme above have been examined, all however without the desired end-result, i.e. homozygous, N. ribisnigri-resistant plants without CRA symptoms.

Example 2

Detection of Recombinants After Pre-selection with AFLP Markers

L. sativa L. plants according to the invention were obtained starting from a single hycross between a plant of the N. ribisnigri-resistant line IVT 793202 issued by the former Institute for Horticultural Plant Breeding and a plant from the butterhead lettuce variety "Ultra RZ". Seed was produced of an F1-plant from this cross. F2 seeds of this cross were sown and F3 seed was produced from a number of plants.

Of this cross 140 plants of an F3 line segregating for resistance (originating from one F2 plant heterozygous for the Nr gene) were then tested for resistance. Of the tested plants 95 were resistant, 32 susceptible, while for 3 plants no clear resistance score was obtained. From the F3 plants with an unambiguous resistance score, leaf material was collected for DNA analysis. The starting point for the detection of AFLP markers linked to the Nr gene were in the first instance a test set of DNA of 5 resistant lettuce lines (including the resistant donor-line IVT 793202), 3 susceptible lines (including Ultra RZ), 2 mixtures ("pools") of DNA of varieties susceptible to *N. ribisnigri* and 44 individuals of the above mentioned F3 line from the hybridization between IVT 793202 and Ultra RZ. In this preliminary study one co-dominant AFLP marker was identified which was fully linked to the resistance gene in the set of 44 plants. With this co-dominant marker homozygously and heterozygously resistant plants can be distinguished.

With the above mentioned co-dominant AFLP marker a total of 121 F3 plants from the hybridization between IVT 793202 and Ultra RZ were subsequently examined. It was thus possible to differentiate the F3 plants into 35 homozygously resistant, 60 heterozygously resistant and 26 susceptible. DNA of the homozygously resistant plants and of the homozygously susceptible plants were pooled separately. From this "resistant" and "susceptible" pool 96 AFLP fingerprints were made. This produced about 4300 AFLP bands, of which 110 were linked to the Nr gene and 25 to the susceptible allele at this locus. 19 AFLP markers were chosen herefrom to use for screening for recombination in the vicinity of the Nr gene. Of these 19 markers 14 were linked to the resistance-producing Nr gene and 5 to the "susceptible" allele.

On the basis of the test with the above stated co-dominant AFLP marker, two F3 plants were identified which were heterozygous for the Nr gene. Of F4 seed which was produced on these plants 800 plants per F4 line were sown. Leaf material of these plants was sampled and DNA isolated. DNA of a final total of 1575 F4 plants was used to screen for marker recombination with the 19 chosen AFLP markers. The result of the first determination was that an indication of marker recombination was obtained for 206 plants. These 206 plants were tested once again for the 19 AFLP markers. This finally resulted in a confirmation of a recombination event in the vicinity of the Nr locus for 162 plants.

F5 seed of the 1575 sampled plants was cultivated. F5 seed was obtained from 89 of the 162 plants identified as marker-recombinant on the basis of the AFLP analysis. The 89 F5 lines which resulted herefrom were tested for resistance to *N. ribisnigri* and for phenotype. In these tests a line (94.85338) was found which no longer segregated for resistance (and was therefore homozygously resistant to the Nr gene), but which still segregated for the CRA phenotype. 50 plants of seed number 94.85338 were analysed again with a number of AFLP markers. After analysis with 22 AFLP markers linked to the Nr gene one of these plants was found to be homozygously recombinant for 12 of the 22 markers. F6 seed (line 95.85051) was recovered from this plant. This line was tested once again for phenotype and resistance, and again all plants of this line were found to be resistant to *N. ribisnigri* and all plants of this line had a normal, i.e. non-CRA phenotype.

F7 seed was cultivated from 11 plants of line 95.85051. This resulted inter alia in seed number 96.85123, which was deposited.

I claim:

1. Plants of the Lactuca genus other than *Lactuca virosa* which are resistant to the aphid *Nasonovia ribisnigri* due to introgression into the genome of the *Lactuca virosa* Nr resistance gene, wherein the genetic information responsible for the CRA phenotype is absent from the genome of the plant or the CRA phenotype is not expressed.

2. Plants as claimed in claim 1, wherein the Nr resistance gene is homozygous.

3. Plants as claimed in claim 1, wherein the plants are lettuce plants of the species *Lactuca sativa* L.

4. Plants as claimed in claim 1, obtained by the following steps of:
   a) selecting a parent plant which is heterozygous for Nr resistance;
   b) manufacturing a segregating population by one of self pollination, cross pollination and a double haploid technique;
   c) producing progeny of the segregating population;
   d) testing the progeny for resistance and CRA phenotype;
   e) selecting suitable progeny plants which are either resistant or which have no CRA phenotype;
   f) producing seed from these plants by self-pollination and culturing progeny from this seed in order to obtain a line; and
   g) testing the line for resistance and CRA phenotype and selecting lines which are uniformly resistant and which uniformly have a non-CRA phenotype.

5. Plants as claimed in claim 4, wherein the segregating population is produced by self-pollination of the parent plant or by crossing of the parent plant with a resistant plant.

6. Plants as claimed in claim 4, wherein the suitable progeny from step e) is one where the plants either are uniformly resistant to *N. ribisnigri* and do not all have the CRA phenotype or uniformly do not have the CRA phenotype and are not all susceptible to *N. ribisnigri*.

7. Plants as claimed in claim 4, wherein the suitable progeny from step e) is one where the plants are both uniformly resistant to *N. ribisnigri* and uniformly do not have the CRA phenotype.

8. Plants as claimed in claim 4, wherein the testing in step d) is based on the absence of a CRA phenotype visible to the eye.

9. Plants as claimed in claim 4, wherein prior to step c), by means of molecular biological techniques a pre-selection is made of plants wherein a recombination event has taken place between the genetic information for the resistance and the genetic information for the CRA phenotype.

10. Plants as claimed in claim 9, wherein the molecular biological techniques are formed by the AFLP technique.

11. Progeny of plants as claimed in claim 1 obtained in generative or vegetative manner, wherein said progeny retain the Nr resistance phenotype and the CRA phenotype is not expressed.

12. Parts or derivatives of plants as claimed in claim 11, which are suitable for propagation, selected from the group consisting of leaves, stems, roots, shoots, protoplasts, somatic embryos, anthers, petioles, cells in culture and seeds, wherein said parts or derivatives retain the Nr resistance phenotype and the CRA phenotype is not expressed.

13. Parts or derivatives of plants as claimed in claim 1, which are suitable for consumption, wherein said parts or derivatives retain the Nr resistance phenotype and the CRA phenotype is not expressed.

* * * * *

UNITED STATES PATENT AND TRADEMARK OFFICE
CERTIFICATE OF CORRECTION

PATENT NO. : 5,977,443
DATED : November 2, 1999
INVENTOR(S) : Johannes Petrus Antonius Jansen It is certified that error appears in the above-identified patent and that said Letters Patent is hereby corrected as shown below:

Column 6 Line 3 before "National" insert --(--.

Column 7 Line 1 "Mterials" should read --Materials--.

Column 7 Line 42 "P2 plants" should read --F2 plants--.

Column 12 Line 52, Claim 12, "in claim 11" should read --in claim 1--.

Signed and Sealed this

Twenty-second Day of August, 2000

Attest:

Q. TODD DICKINSON

*Attesting Officer*     *Director of Patents and Trademarks*